(12) United States Patent
Waechter-Stehle et al.

(10) Patent No.: US 12,127,888 B2
(45) Date of Patent: Oct. 29, 2024

(54) INTELLIGENT ULTRASOUND SYSTEM

(71) Applicant: KONINKLIJKE PHILIPS N.V., Eindhoven (NL)

(72) Inventors: Irina Waechter-Stehle, Hamburg (DE); Frank Michael Weber, Hamburg (DE); Christian Buerger, Hamburg (DE); Thomas Heiko Stehle, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 156 days.

(21) Appl. No.: 16/489,121

(22) PCT Filed: Feb. 28, 2018

(86) PCT No.: PCT/EP2018/054865
§ 371 (c)(1),
(2) Date: Aug. 27, 2019

(87) PCT Pub. No.: WO2018/158283
PCT Pub. Date: Sep. 7, 2018

(65) Prior Publication Data
US 2020/0060660 A1 Feb. 27, 2020

(30) Foreign Application Priority Data
Feb. 28, 2017 (EP) .................... 17158367

(51) Int. Cl.
*A61B 8/00* (2006.01)
*A61B 8/08* (2006.01)
*A61B 8/12* (2006.01)

(52) U.S. Cl.
CPC ............... *A61B 8/585* (2013.01); *A61B 8/12* (2013.01); *A61B 8/4438* (2013.01);
(Continued)

(58) Field of Classification Search
CPC ......... A61B 8/585; A61B 8/12; A61B 8/4438; A61B 8/4488; A61B 8/466; A61B 8/469; A61B 8/483; A61B 8/5292
See application file for complete search history.

(56) References Cited

U.S. PATENT DOCUMENTS 4,459,853 A 7/1984 Miwa et al.
5,967,985 A 10/1999 Hayakawa
(Continued)

FOREIGN PATENT DOCUMENTS

EP 3117775 A1 1/2017
JP 2006326084 A 12/2006
(Continued)

OTHER PUBLICATIONS

International Search Report for International Application No. PCT/EP2018/054865, filed Feb. 28, 2018, 5 pages.
(Continued)

*Primary Examiner* — Joel Lamprecht
*Assistant Examiner* — Ashish S Jasani

(57) ABSTRACT

The invention relates to an ultrasound system for imaging a volumetric region comprising a region of interest (ROI). The system comprises a probe; an ultrasound wave controlling unit adapted to control ultrasound wave transmission and provide ultrasound image data of the volumetric region; an image processor; and a ROI identifier, which is adapted to generate identification data indicating the ROI within the volumetric region; wherein the ultrasound wave transmission is configurable by a plurality of use cases in response to respective identifiers of said use cases, each use case being associated with a particular imaging procedure and comprising an anatomical model for said imaging procedure; and wherein the ROI identifier is configurable by the
(Continued)

respective anatomical models of said use cases. A method of configuring such an ultrasound system is also disclosed.

2 Claims, 8 Drawing Sheets

(52) U.S. Cl.
CPC ............ *A61B 8/4488* (2013.01); *A61B 8/466* (2013.01); *A61B 8/469* (2013.01); *A61B 8/483* (2013.01); *A61B 8/5292* (2013.01); *A61B 8/0883* (2013.01)

(56) References Cited

U.S. PATENT DOCUMENTS

| | | | |
|---|---|---|---|
| 6,123,670 A | 9/2000 | Mo | |
| 2003/0045795 A1* | 3/2003 | Bjaerum | G01S 7/52074 600/441 |
| 2004/0254439 A1* | 12/2004 | Fowkes | G16H 50/20 600/407 |
| 2007/0055153 A1* | 3/2007 | Simopoulos | G16H 30/40 600/437 |
| 2007/0167801 A1 | 7/2007 | Webler et al. | |
| 2008/0020714 A1* | 1/2008 | Mezhinsky | A61B 90/90 455/73 |
| 2010/0292577 A1 | 11/2010 | Sato et al. | |
| 2011/0040176 A1 | 2/2011 | Razansky et al. | |
| 2011/0246129 A1* | 10/2011 | Ishikawa | A61B 8/4245 702/150 |
| 2012/0071758 A1 | 3/2012 | Lachaine et al. | |
| 2012/0163124 A1 | 6/2012 | Akiyama et al. | |
| 2012/0232386 A1 | 9/2012 | Mansi et al. | |
| 2015/0005621 A1 | 1/2015 | Liu | |
| 2015/0011886 A1 | 1/2015 | Radulescu | |
| 2015/0216510 A1 | 8/2015 | Lee | |
| 2016/0066883 A1* | 3/2016 | Mickelsen | A61B 8/12 600/463 |
| 2016/0174934 A1* | 6/2016 | Cong | A61B 8/4254 600/459 |
| 2017/0360399 A1* | 12/2017 | Rothberg | B06B 1/0622 |
| 2018/0168539 A1* | 6/2018 | Singh | A61B 8/4483 |
| 2018/0246208 A1* | 8/2018 | Dittmer | G01S 7/52084 |
| 2018/0306919 A1* | 10/2018 | Van Rens | G01S 7/52073 |

FOREIGN PATENT DOCUMENTS

| | | |
|---|---|---|
| JP | 2009039232 A | 2/2009 |
| JP | 2011139722 A | 7/2011 |
| JP | 2014050674 A1 | 3/2014 |
| WO | 00/04831 A1 | 2/2000 |
| WO | 2012061940 A1 | 5/2012 |
| WO | 2014097090 A1 | 6/2014 |
| WO | 2014139032 A1 | 9/2014 |
| WO | 2014162232 A1 | 10/2014 |
| WO | 2015028949 A2 | 3/2015 |

OTHER PUBLICATIONS

Written Opinion of the International Searching Authority for International Application No. PCT/EP2018/054865, filed Feb. 28, 2018, 7 pages.

Schneider, et al., "Automation with Anatomical Intelligence as a Novel Pathway in Echocardiography for the Advancement of Measurements and Analysis", Current Cardiovascular Imaging Reports, vol. 8, No. 12, Oct. 14, 2015, pp. 1-8.

Tsang, et al., "Transthoracic 3D Echocardiographic Left Heart Chamber Quantification Using an Automated Adaptive Analytics Algorithm", JACC: Cardiovascular Imaging, vol. 9, No. 7, Jan. 1, 2016, pp. 769-782.

Loschak, et al., "Algorithms for Automatically Pointing Ultrasound Imaging Catheters", IEEE Transactions on Robotics, vol. 33, No. 1, Feb. 1, 2017, pp. 81-91.

Ecabert, et al. "Automatic model-based segmentation of the heart in CT images." Medical Imaging, IEEE Transactions on Medical Imaging, vol. 27, Issue 9, Sep. 2008, pp. 1189-1201. (Abstract).

Winder, et al., "Synthetic Structural Imaging (Ssi): A New Ultrasound Method for Tracking Breast Cancer Morphology", Proceedings of the 39th Annual Symposium of the Ultrasonic Industry Association, Apr. 12-14, 2010, 4 pages.

* cited by examiner

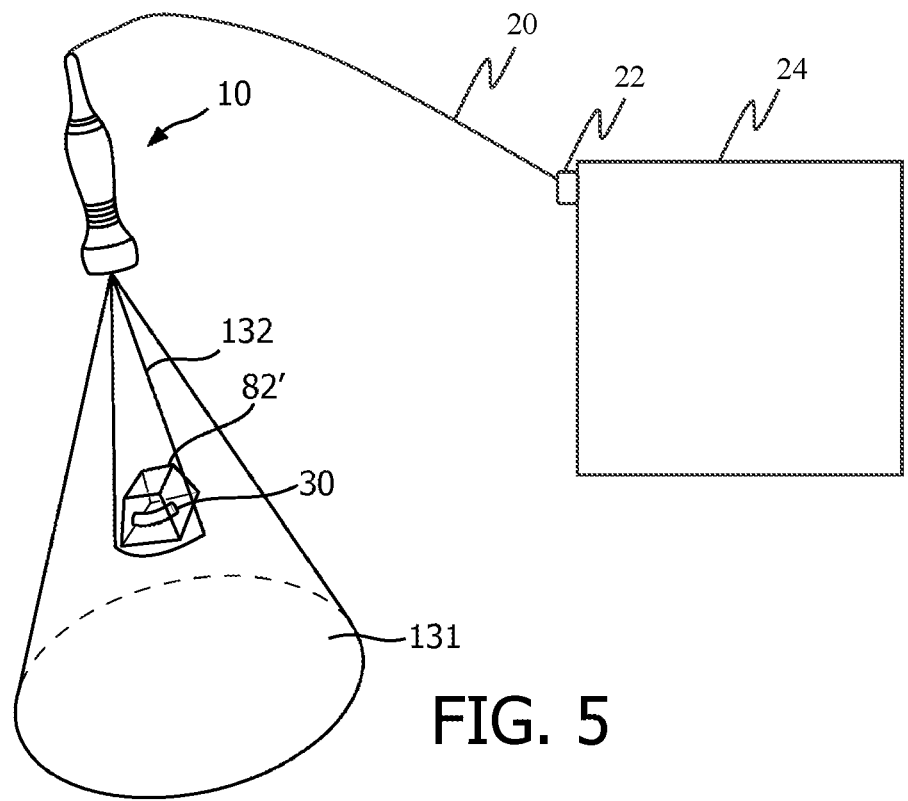
FIG. 5
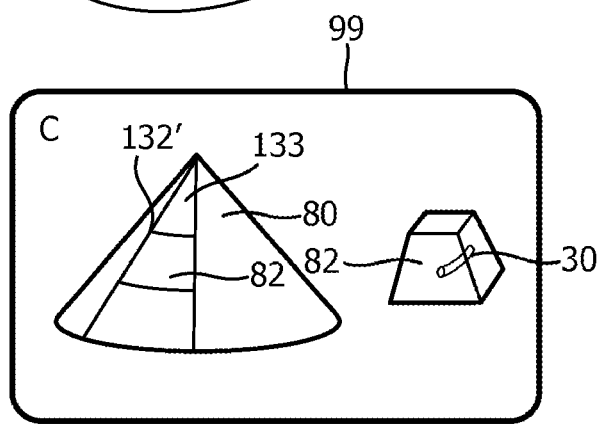
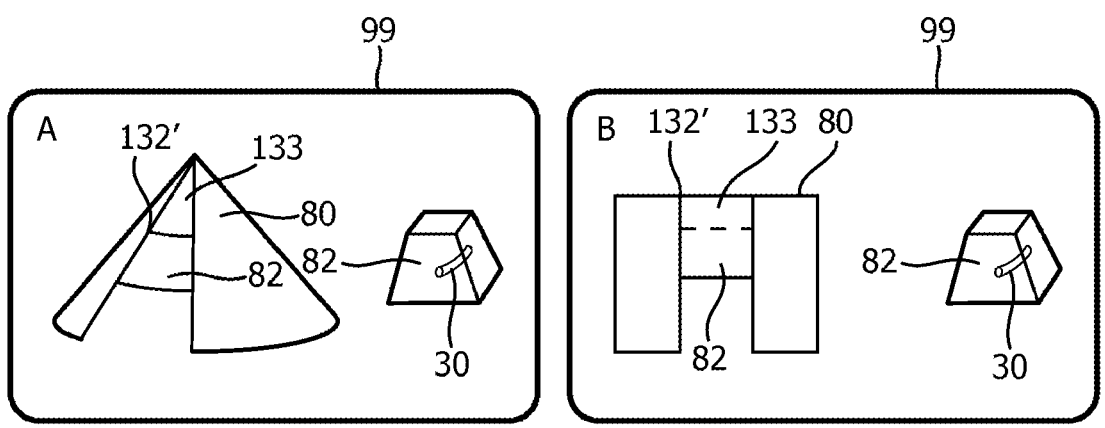
FIG. 6

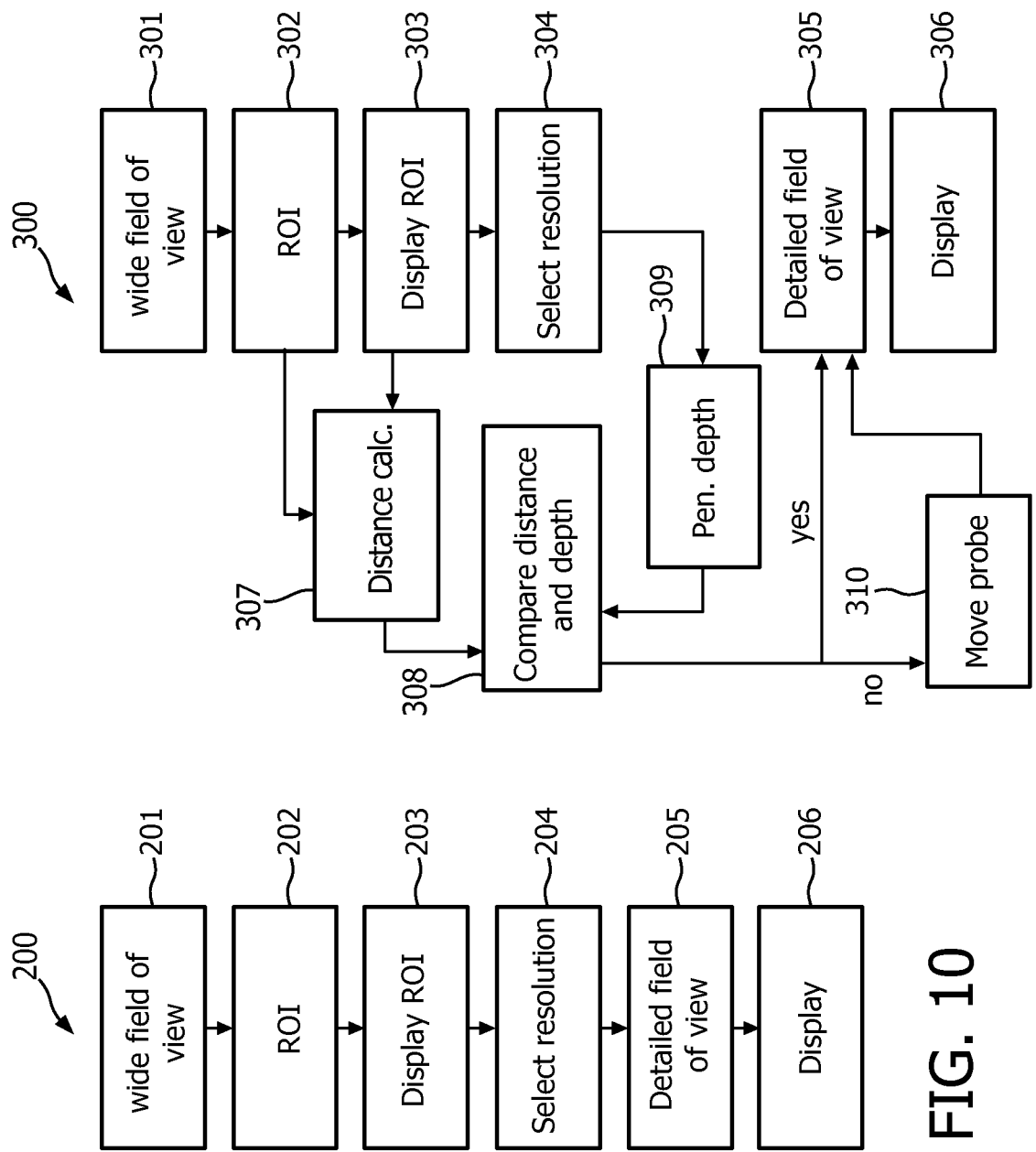

INTELLIGENT ULTRASOUND SYSTEM

RELATED APPLICATIONS

This application is the U.S. National Phase application under 35 U.S.C. § 371 of International Application No. PCT/EP2018/054865, filed on Feb. 28, 2018, which claims the benefit of European Application No. 17158367.7, filed Feb. 28, 2017. This application is hereby incorporated by reference herein.

FIELD OF THE INVENTION

The invention relates to an ultrasound system for imaging a volumetric region comprising a region of interest comprising: a probe with an ultrasound array; a ultrasound wave controlling unit coupled to the array and adapted to control the ultrasound wave transmission and provide ultrasound image data of the volumetric region; and an image processor responsive to the ultrasound image data, based on which it is adapted to produce an ultrasound image.

The present invention further relates to a method of configuring such an ultrasound system.

BACKGROUND OF THE INVENTION

Ultrasound waves find several applications in medicine. One such application is ultrasound imaging, wherein ultrasound waves are emitted by an ultrasound device comprising an array of ultrasound transducers into the body of a patient and echoes of the ultrasound waves are collected by the ultrasound transducers or by dedicated ultrasound receivers and processed to generate an ultrasound image, e.g. a 1D, 2D or 3D ultrasound image. Such ultrasound systems typically comprise an ultrasound transducer array, e.g. as part of an ultrasound probe, for delivering ultrasound waves to a subject, e.g. to a patient being imaged or treated. Such an ultrasound transducer array typically comprises a plurality of ultrasound transducers such as piezoelectric transducer elements formed of materials such as lead zirconate titanate (PZT) or polyvinylidenefluoride (PVDF) and capacitive micro-machined ultrasonic transducer (CMUT) elements in which a membrane including a first electrode over a cavity comprising a second electrode opposite the first electrode and separated therefrom by the cavity is used to generate the ultrasound waves (or receive the ultrasound waves in a receive mode) through application of an appropriate stimulus, e.g. an alternating current, to the first and second electrodes. An ultrasound imaging system with a CMUT transducer probe is known from WO2015028314 A1. This probe comprises an array having CMUT cells arranged to operate in either of the following modes: a conventional mode, wherein a DC bias voltage sets a CMUT membrane of the cell to vibrate freely above a cell floor during operation of the CMUT cell; and a collapsed mode, wherein the DC bias voltage sets the CMUT membrane of the cell to be collapsed to the cell floor during operation of the CMUT cell. An increase in the DC bias voltage results in an increase in a center frequency of the frequency response of the CMUT cell during the operation the collapsed mode, and a decrease in the DC bias voltage results in a decrease in the center frequency of the frequency response of the CMUT cell during the operation in the collapsed mode. The DC bias voltage can be selected for different clinical applications depending on the frequency at which a volumetric region of the body is imaged.

Such volumetric (3D or 4D) imaging for example is used in invasive ultrasound imaging techniques such as intra-cardiac echography (ICE) and intra-vascular ultrasound (IVUS) procedures (for example, during pull back acquisition), in which the ultrasound probe may take the shape of a catheter and may be inserted into the patient to investigate a region of interest, and in some cases, to perform a procedure in the region of interest (ROI), either with a surgical instrument attached to the ultrasound probe or with a separate surgical instrument, in which case the ultrasound probe may be used to image the surgical instrument within the region of interest, e.g. to provide visual feedback to an operator of the instrument to ensure that the instrument is correctly applied to the ROI. To this end, the ultrasound system may be deployed with so-called anatomical intelligence, which facilitates the automated detection of the ROI using an appropriate anatomical model, such as for example a heart model in case of ICE procedures. Such models typically deploy one or more segmentation algorithms that evaluate the (volumetric) ultrasound image data captured by the ultrasound probe and identify the anatomical feature within this data, e.g. by evaluation of pixel (or voxel) brightness and contrast levels between adjacent (groups of) pixels (or voxels). The model is thus mapped onto the identified anatomical structure, such that anatomical parameters of interest, e.g. anatomy dimensions, anatomy function such as cardiac ejection fraction estimation, and so on, can be automatically derived from the (volumetric) ultrasound image data, thereby improving inter-operator consistency between obtained results and making the system easier to use for less experienced operators.

A remaining problem is that where the ultrasound system may be used for different medical procedures, for example invasive techniques, it can be difficult for its operator, in particular a less experienced operator, to correctly configure and operate the ultrasound system.

SUMMARY OF THE INVENTION

It is an object of the present invention to provide an ultrasound system, which facilitates ease of use by its operator.

This object is achieved according to the invention by providing an ultrasound system for imaging a volumetric region comprising a region of interest comprising a probe having an ultrasound transducer array; an ultrasound wave controlling unit to the array and adapted to control ultrasound wave transmission and provide ultrasound image data of the volumetric region; an image processor responsive to the ultrasound image data, based on which it is adapted to produce an ultrasound image; and a region of interest (ROI) identifier enabling to identify a region of interest on the basis of the ultrasound image data, and which identifier is adapted to generate identification data indicating the region of interest within the volumetric region; wherein the ultrasound wave transmission is configurable by a plurality of use cases in response to respective identifiers of said use cases, each use case being associated with a particular imaging procedure and comprising an anatomical model for said imaging procedure; and wherein the ROI identifier is configurable by the respective anatomical models of said use cases.

Such an ultrasound system may be (semi-)automatically configured in accordance with settings that are specific to a particular imaging procedure, which facilitates the use of such a system by less experienced users and reduces the time required to configure the system, thereby facilitating a higher patient throughput whilst at the same time improving the accuracy of anatomical parameters retrieved from volumetric imaging data captured in such procedures. Depending on the particular imaging procedure the ultrasound wave controlling unit, in response to the respective identifiers of the use cases, is adapted to be configured by the plurality of use cases and can adapt the ultrasound array to transmit an ultrasound wave, characteristics of which are optimized to acquire ultrasound image data for the respective anatomical model.

In an embodiment of the present application, the ultrasound wave controlling unit comprises a beamformer arranged to control ultrasound beam steering of the transmitted ultrasound wave.

In another embodiment, the probe is suitable for intracavity imaging and each use case is associated with a particular intracavity imaging procedure and according anatomical model.

In a further embodiment, the ultrasound system further comprises a drive mechanism coupled to the probe and the ROI identifier, which drive mechanism acts to move the probe during operation under control of the ROI identifier. In this manner, the ROI identifier may control the drive mechanism to move the probe into a target location relative to the ROI as specified in the use case with which the ultrasound system is configured, e.g. an optimal distance from the ROI for its imaging or for facilitating an interventional procedure in the ROI. This embodiment may be particular beneficial for low-skilled users, since the ultrasound imaging system is arranged based on the identified use case and associated to the selected anatomy model, to assess an optimal ultrasound wave transmission applicable for the given probe's location. If no optimal configuration can be achieved the drive mechanism will move the probe to an improved location with respect to the ROI.

In an embodiment, the probe comprises a cable including a plug for connecting to a user console of the ultrasound system, wherein the plug comprises a tag storing the identifier of a particular use case associated with the probe; and the user console comprises a reader of said tag adapted to retrieve said identifier for configuring the ultrasound system in accordance the particular use case. In this way, the appropriate use case may be automatically detected, which for instance is particularly suitable where the probe 10 is used in a single procedure only, as for instance often is the case with IVUS probes.

Alternatively, the ultrasound system further comprises a user interface adapted to receive a user-specified identifier of a particular use case. This may be more appropriate where a probe may be used in different invasive procedures, e.g. different ICE procedures.

In another embodiment, the ultrasound system is configured to generate guidance instructions for assisting a user of the probe in guiding the probe to a target location associated with the ROI in response to the ROI identifier. For example, the ultrasound system may be adapted to generate said guidance instructions based on a determined distance of the probe to the ROI. This therefore assists the controller of the probe to guide the probe to a desired (target location), which makes it easier for the controller to control the probe. This embodiment may be further beneficial for low-skilled users, since the ultrasound imaging system is arranged based on the identified use case and associated to the selected anatomy model, to assess an optimal ultrasound wave transmission applicable for the given probe's location. If no optimal configuration can be achieved the guidance instructions will be generated by the system in order to assist the user to move the probe to an improved location with respect to the ROI.

In an example embodiment, the probe comprises an array of CMUT transducers adapted to steer ultrasound beams in a variable frequency range over the volumetric region; and the ultrasound system further comprises a transducer frequency controller coupled to the beamformer and adapted to vary operation frequencies of the CMUT transducers within the frequency range; which frequency controller is arranged to set the operation frequency to a first frequency for the ultrasound beam steered in the volumetric region.

This example embodiment uses variable frequency capabilities of the CMUT transducers in providing a new imaging technique that allows increasing the frequency of the ultrasound beams within the identified region of interest. Once the ROI is identified in the ultrasound data by the ROI identifier, the transducer frequency controller increases the beam frequencies in a portion of the volumetric region in which the ROI is located. Further, the system permits the intracavity probes to be moved with respect to the volumetric region giving additional flexibility to the user during the ultrasound imaging by automatically adjusting the probe's position with respect to the volumetric region depending on the location of the identified ROI within the region. If the distance between the identified ROI and the probe is larger than the penetration depth of the acoustic beams at the selected increased frequency the system may arrange the drive mechanism to move the probe closer to the ROI, such that the detail view of the ROI with increased beam frequency may be produced.

In an embodiment, the beamformer provides the ultrasound image data having a relatively low spatial resolution within the volumetric region and relatively high spatial resolution within the region of interest.

In this embodiment increasing of the beam frequency transmitted over the region of interest allows the beamformer receiving the higher frequency echo signals originating from the ROI; thus, providing a higher resolution ultrasound data of the identified ROI. Compared to the prior art systems the ultrasound system of the present invention is capable of receiving more detailed ultrasound information on the volumetric region during an ultrasound scan.

In a further embodiment, the image processor produces a wide view of the volumetric region based of the low spatial resolution data and a detail view of the region of interest based on the high spatial resolution data.

Acoustic wave attenuation increases with increasing frequency. Therefore, it may be beneficial producing the wide view of the volumetric region with larger penetration depth but reduced spatial resolution and the detailed field view within the wide field of view, wherein the ROI can be imaged with higher spatial resolution. The advantage of the present invention that both fields of view can be produced using the same CMUT transducer array during a single ultrasound scan.

In another embodiment, the ultrasound system further comprises an image display coupled to the image processor, which displays both the wide view of the volumetric region and the detail view of the region of interest.

Both fields of view may be displayed to a user either next to each other as separate ultrasound images or in a spatial registration as one ultrasound image.

In yet another embodiment the ultrasound system further comprises a user interface coupled to the ROI identifier and responsive to a manual selection of the ROI within the volumetric region.

This gives the user an opportunity to manually select the ROI to be identified by the ROI identifier. Optionally, the user interface can be also coupled to the frequency control, such that the user can also select the relatively low and high frequencies of the beams steered within the volumetric region and within the region of interest correspondingly.

In a further embodiment the array is a two-dimensional array or one-dimensional array.

Depending on the array's design the ultrasound system may be providing the three dimensional ultrasound images or two dimensional ultrasound images (2D slices) of the volumetric region.

According to another aspect, there is provided an ultrasound system module for imaging a volumetric region comprising a region of interest and adapted for connection to a probe suitable for intracavity imaging; said module comprising a beamformer for coupling to the array and adapted to control ultrasound beam steering and provide ultrasound image data of the volumetric region; an image processor responsive to the ultrasound image data, based on which it is adapted to produce an ultrasound image; and a region of interest (ROI) identifier enabling to identify a region of interest on the basis of the ultrasound image data, and which identifier is adapted to generate identification data indicating the region of interest within the volumetric region; wherein the ultrasound system is configurable by a plurality of use cases in response to respective identifiers of said use cases, each use case being associated with a particular intracavity imaging procedure and comprising an anatomical model for said intracavity imaging procedure; and wherein the ROI identifier is configurable by the respective anatomical models of said use cases.

BRIEF DESCRIPTION OF THE DRAWINGS

In the drawings:

FIG. 5 illustrates the scanning of the volumetric region with a relatively low frequency of the ultrasound beams steered within the volumetric region outside of the region of interest and a relatively high frequency of the ultrasound beams steered within the region of interest;

FIG. 6a, 6b and 6c illustrate displays of ultrasound images of a volumetric region together with the wide view of the volumetric region comprising the detail view of the region of interest;

FIG. 10 illustrates a workflow of a basic principle of variable frequency image acquisition according to an example embodiment of the present invention;

FIG. 11 illustrates a workflow for variable frequency image acquisition in accordance with an example embodiment the present invention.

DETAILED DESCRIPTION OF EMBODIMENTS

Figure 1:
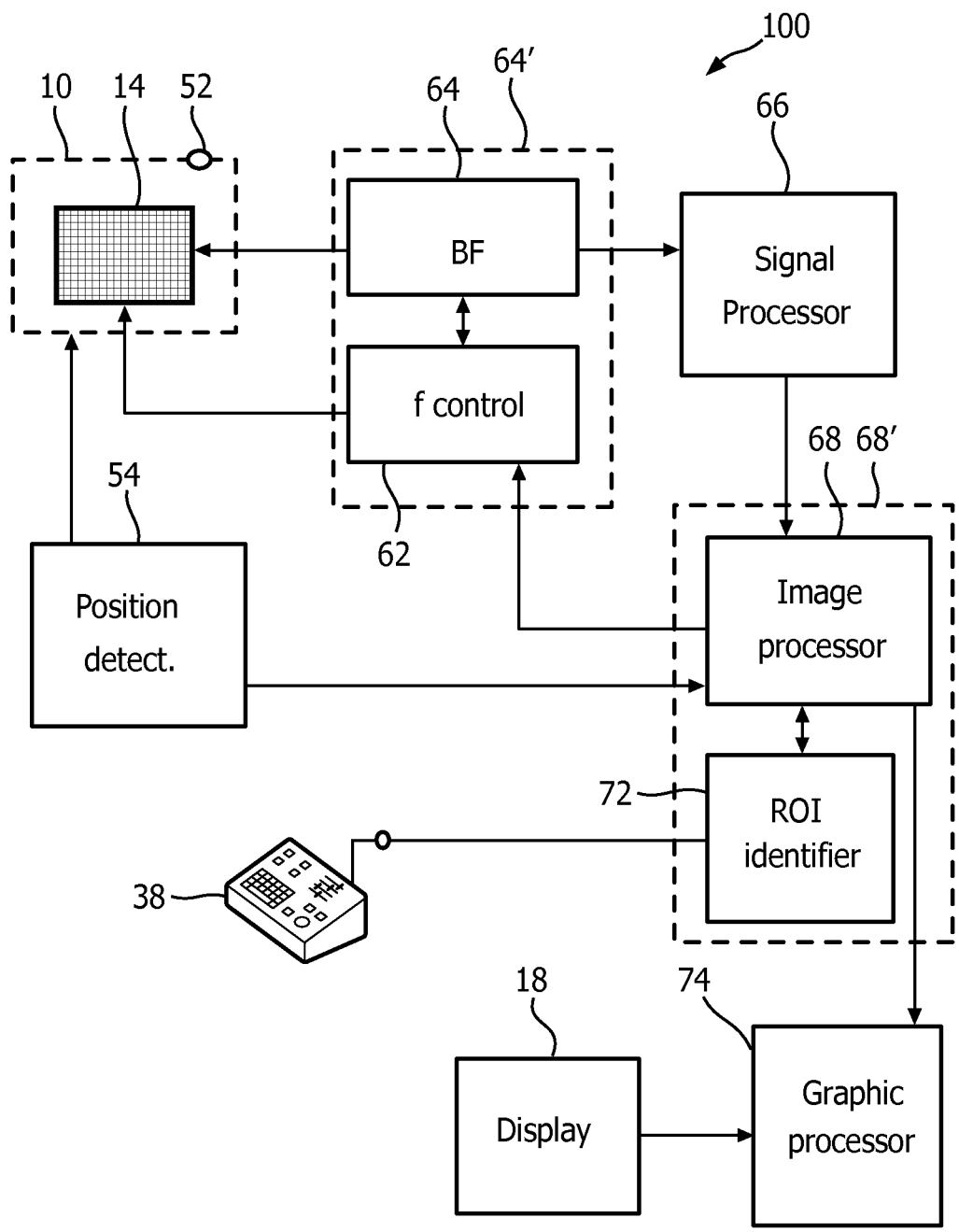
FIG. 1 illustrates an ultrasound system for variable frequency imaging of a volumetric region in accordance with the principles of the present invention.

FIG. 1 shows schematically and exemplarily an ultrasound system 100 for in accordance with the principles of the present invention. A probe 10 may comprise an array 14 ultrasound transducers for imaging a volumetric region within a patient. Any suitable type of ultrasound transducers may be deployed in such an array. The probe 10 may be adapted for invasional ultrasound procedures, such as ICE or IVUS procedures. For example, the probe 10 may take the shape of a catheter or the like for such procedures. The array 14 can be either a two dimensional or a one dimensional array. In a particular embodiment, the array 14 is adapted for variable frequency imaging of the volumetric region, e.g. using variable frequency ultrasound transducers such as for example capacitive micromachined ultrasound transducers (CMUTs). The CMUTs of the array transmit ultrasound beams in a variable frequency range over a volumetric field of view 131 (FIG. 5) (comprising the volumetric region) and receive echoes in response to the transmitted beams. The transducers of the array 14 transducer are coupled to a beamformer 64, which controls a steering of the ultrasound beams transmitted by the transducers, e.g. CMUTs by way of non-limiting example, of the array transducer 14. The beamformer further beamforms echoes received by the transducers. Beams may be steered straight ahead from (orthogonal to) the transducer array 14, or at different angles for a larger field of view. Further, the beamformer 64 can also control a density and distribution of the steered beams within the volumetric region. Optionally, the ultrasound system may have a plurality of microbeamformers (not shown) each coupling groups of the individual transducers with the beamformer 64. The microbeamformers (sub-array beamformer) partially beamforms the signals from the groups of the transducers thereby reducing amount of signal channels coupling the probe and main acquisition system. The microbeamformers are preferably fabricated in integrated circuit form and located in the housing of the probe 10 near the array transducer. The probe 10 may further include a position sensor 52 which provides signals indicative of the position of the probe 10 to a transducer position detector 54. The sensor 52 may be a magnetic, electromagnetic, radio frequency, infrared, or other type of sensor.

The partially beamformed signals produced by the microbeamformers are forwarded to a beamformer 64 where partially beam-formed signals from individual groups of transducers are combined into a fully beam-formed signal. The ultrasound system 100 further comprises a transducer frequency controller 62 coupled to the array 14 and the beamformer 64 (or optionally to the plurality of microbeamformers). The frequency controller 62 controls the frequency of the transmitted and received ultrasound beams via adjusting a resonance frequency of each transducer in the array 14, as will be described more detailed below for CMUT transducers. The fully beam-formed signal (i.e. coherent echo signals along the beams) represent ultrasound image data, which are processed by filtering, amplitude detection, Doppler signal detection, and other processes by a signal processor 66. The ultrasound data are then processed into ultrasound image signals in the coordinate system of the probe (r,θ,φ for example) by an image processor 68. The ultrasound image signals may be further converted to a desired ultrasound image format (x,y,z Cartesian coordinates, for example) by a graphic processor 74 and displayed on a display 18.

A region of interest identifier 72 is coupled to the image processor 68 and, based on analyses of the ultrasound image data, is adapted to generate identification data indicating a region of interest 82' (ROI) within the volumetric field of view 131. Both the image processor 68 and the ROI identifier 72 can be a part of one image analyses unit 68'. The ultrasound imaging system 100 may be controlled by a user interface 38. In particular the user interface 38 can be connected to the ROI identifier 72 or directly to the image analyses unit 68' permitting a manual selection of the ROI 82' based on the ultrasound image displayed on the display. Further, a user via the user interface 38 also select a desired frequency within a variable frequency range of the array, with which the user wishes the ROI to be imaged in case of a variable frequency array 14. Alternatively, the user can be given a selection of a desired resolution ranges, with which the user wishes the ROI to be imaged. This user input, such as location and size of the ROI 82' within the volumetric field of view 131 and the desired ROI imaging frequency or the resolution range, in a shape of the identification data is communicated by the image analyses unit 68' to the transducer frequency controller 62. In the present embodiment the user identified parameters are exchanged between the ROI identifier and the image processer 68, wherein the image processor computes coordinates of the ROI 82' and a volumetric region 132 (illustrated in FIG. 5) surrounding the identified ROI in the volumetric field of view 131 based on the generated identification data provided by the ROI identifier. The transducer frequency controller 62 as well as the beamformer 64 are responsive to the identification data generated by the ROI identifier 72 and processed by the image processor 68. In a particular embodiment, in which the operating frequency of the array 14 is adjustable, the transducer frequency controller 62 together with the beamformer adjusts the frequency of the beams steered within the volumetric region 132 surrounding the identified ROI in the volumetric field of view 131. In another embodiment, in which the resolution of the steered beams is adjustable, the transducer frequency controller 62 together with the beamformer can vary the density of the beams steered within the volumetric region 132. The beamformer and the transducer frequency controller can be designed as one ultrasound wave controlling unit 64' combining the frequency variation and beamforming capabilities. In the alternative embodiment, the microbeamformer may be combined together the transducer frequency controller 62 into the ultrasound wave controlling unit 64' and may be located within a housing of the probe. In yet another alternative embodiment the ultrasound wave controlling unit (64') may be arranged to control the array to transmit a divergent ultrasound wave. Depending on the array's technical specifications either a frequency and/or density of the transmitted waves (in the particular embodiment, steered beams) can be controlled by the beamformer 64 (or by the ultrasound wave controlling unit 64'). It may be beneficial for the user to have reduced the density of the ultrasound beams steered outside of the ROI, thereby providing an increased frame rate of acquired ultrasound data from the volumetric region. This increase of the overall frame rate might result in the reduced resolution of the anatomy features located within the volumetric region but outside of the ROI. The optimal resolution and/or frame rate of the given anatomy (defined by the medical procedure) may be linked to the location of the ROI and its relative position from the probe within the volumetric region.

In the particular embodiment of the present invention the variation of the imaging frequency of the ultrasound system is provided using CMUT transducers adapted to operate in a collapsed mode. CMUT technology allows the tuning of the imaging frequency by changing the bias voltage. This frequency range extends over a broad range and on top of this range at each frequency there is also a bandwidth which for a substantial part is close to 100%. This large frequency variability allows for imaging over a wide range of penetrations and resolutions. However, it should be understood that other types of arrays 14 may be deployed in which different regions of the volumetric image may be imaged at different resolutions, as for instance is explained in U.S. Pat. No. 6,123,670.

Where the array 14 of the ultrasound system of the present invention is a CMUT array, the array typically comprises a plurality of CMUT cells (transducers). Each CMUT cell 103 typically comprises a flexible membrane or diaphragm 114 suspended above a silicon substrate 112 with a gap or cavity 118 there between. A top electrode 120 is located on the diaphragm 114 and moves with the diaphragm. A bottom electrode is located on the floor of the cell on the upper surface of the substrate 112 in this example. Other realizations of the electrode 120 design can be considered, such as electrode 120 may be embedded in the membrane 114 or it may be deposited on the membrane 114 as an additional layer. In this example, the bottom electrode 122 is circularly configured and embedded in the substrate layer 112 by way of non-limiting example. Other suitable arrangements, e.g. other electrode shapes and other locations of the bottom electrode 122, e.g. on the substrate layer 112 such that the bottom electrode 122 is directly exposed to the gap 118 or separated from the gap 118 by an electrically insulating layer or film to prevent a short-circuit between the top electrode 120 and the bottom electrode 122. In addition, the membrane layer 114 is fixed relative to the top face of the substrate layer 112 and configured and dimensioned so as to define a spherical or cylindrical cavity 118 between the membrane layer 114 and the substrate layer 112. It is noted for the avoidance of doubt that in FIG. 2 the bottom electrode 122 is grounded by way of non-limiting example. Other arrangements, e.g. a grounded top electrode 120 or both top electrode 120 and bottom electrode 122 floating are of course equally feasible.

The cell 103 and its cavity 118 may exhibit alternative geometries. For example, cavity 118 could exhibit a rectangular or square cross-section, a hexagonal cross-section, an elliptical cross-section, or an irregular cross-section. Herein, reference to the diameter of the CMUT cell 103 shall be understood as the biggest lateral dimension of the cell.

The bottom electrode 122 may be insulated on its cavity-facing surface with an additional layer (not pictured). An electrically insulating layer is an oxide-nitride-oxide (ONO) dielectric layer formed above the substrate electrode 122 and below the membrane electrode 120 although it should be understood any electrically insulating material may be contemplated for this layer. The ONO-dielectric layer advantageously reduces charge accumulation on the electrodes which leads to device instability and drift and reduction in acoustic output pressure.

An example fabrication of ONO-dielectric layers on a CMUT is discussed in detail in European patent application EP 2,326,432 A2 by Klootwijk et al., filed Sep. 16, 2008 and entitled "Capacitive micromachined ultrasound transducer." Use of the ONO-dielectric layer is desirable with pre-collapsed CMUTs, which are more susceptible to charge retention than CMUTs operated with suspended membranes. The disclosed components may be fabricated from CMOS compatible materials, e.g., Al, Ti, nitrides (e.g., silicon nitride), oxides (various grades), tetra ethyl oxysilane (TEOS), poly-silicon and the like. In a CMOS fabrication, for example, the oxide and nitride layers may be formed by chemical vapor deposition and the metallization (electrode) layer put down by a sputtering process. Suitable CMOS processes are LPCVD and PECVD, the latter having a relatively low operating temperature of less than 400° C. Exemplary techniques for producing the disclosed cavity 118 involve defining the cavity in an initial portion of the membrane layer 114 before adding a top face of the membrane layer 114. Other fabrication details may be found in U.S. Pat. No. 6,328,697 (Fraser).

Figure 2:
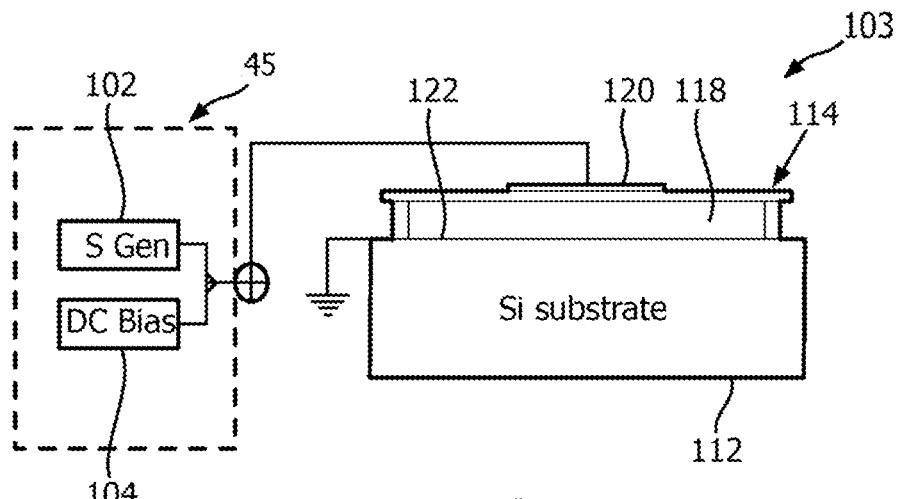
FIG. 2 illustrates a CMUT cell controlled by a DC bias voltage and driven by an r.f. drive signal.

In FIG. 2, the diameter of the cylindrical cavity 118 is larger than the diameter of the circularly configured electrode plate 122. Electrode 120 may have the same outer diameter as the circularly configured electrode plate 122, although such conformance is not required. Thus, the membrane electrode 120 may be fixed relative to the top face of the membrane layer 114 so as to align with the electrode plate 122 below. The electrodes of the CMUT cell 103 provide the capacitive plates of the device and the gap 118 is the dielectric between the plates of the capacitor. When the diaphragm vibrates, the changing dimension of the dielectric gap between the plates provides a changing capacitance which is sensed as the response of the CMUT cell 103 to a received acoustic echo.

The spacing between the electrodes is controlled by applying a static voltage, e.g. a DC bias voltage, to the electrodes with a voltage supply 45. The voltage supply 45 is implemented into the transducer frequency controller 62 and provides its frequency control capabilities. The transducers of the array 14 each may have a separate voltage supply or share several voltage supplies implemented in the transducer frequency controller 62. The voltage supply 45 may also optionally comprise separate stages 102, 104 for providing the DC and AC or stimulus components respectively of the drive voltage of the CMUT cells 103. The first stage 102 may be adapted to generate the static (DC) voltage component and the second stage 104 may be adapted to generate an alternating variable voltage component or stimulus having a set alternating frequency, which signal typically is the difference between the overall drive voltage and the aforementioned static component thereof. The static or bias component of the applied drive voltage preferably meets or exceeds the threshold voltage for forcing the CMUT cells 103 into their collapsed states. This has the advantage that the first stage 102 may include relatively large capacitors, e.g. smoothing capacitors, in order to generate a particularly low-noise static component of the overall voltage, which static component typically dominates the overall voltage such that the noise characteristics of the overall voltage signal will be dominated by the noise characteristics of this static component. Other suitable embodiments of the voltage source supply 45 should be apparent, such as for instance an embodiment in which the voltage source supply 45 contains three discrete stages including a first stage for generating the static DC component of the CMUT drive voltage, a second stage for generating the variable DC component of the drive voltage and a third stage for generating the frequency modulation or stimulus component of the signal, e.g. a pulse circuit or the like. It is summarized that the voltage source supply 45 may be implemented in any suitable manner.

As is known per se, by applying a static voltage above a certain threshold, the CMUT cell 103 is forced into a collapsed state in which the membrane 114 collapses onto the substrate 112. This threshold value may depend on the exact design of the CMUT cell 103 and is defined as the DC bias voltage at which the membrane 114 sticks to (contacts) the cell floor by Van der Waal force during the application of the bias voltage. The amount (area) of contact between the membrane 114 and the substrate 112 is dependent on the applied bias voltage. Increasing the contact area between the membrane 114 and the substrate 112 increases the resonance frequency of the membrane 114, as will be explained in more detail with the aid of FIG. 3a-d.

Figure 3A:
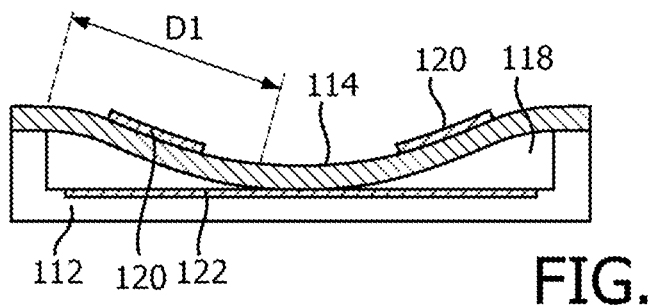
FIGS. 3a-3d illustrate the principles of collapsed mode CMUT operation applied in an implementation of the present invention.
Figure 3B:
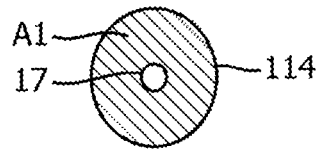
Figure 3C:
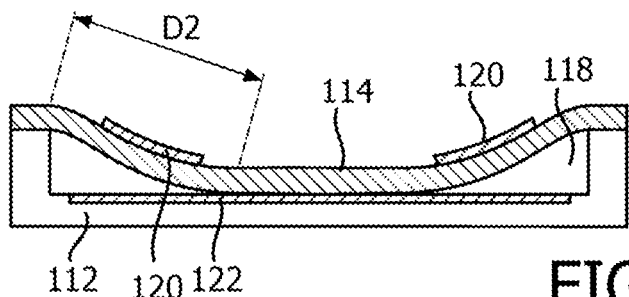

The frequency response of the collapsed mode CMUT cell 103 may be varied by adjusting the DC bias voltage applied to the CMUT electrodes after collapse. As a result, the resonant frequency of the CMUT cell increases as a higher DC bias voltage is applied to the electrodes. The principles behind this phenomenon are illustrated in FIGS. 3a and 3b. The cross-sectional views of FIGS. 3a and 3c illustrate this one-dimensionally by the distances D1 and D2 between the outer support of the membrane 114 and the point where the membrane begins to touch the floor of the cavity 118 in each illustration. It can be seen that the distance D1 is a relatively long distance in FIG. 3a when a relatively low bias voltage is applied, whereas the distance D2 in FIG. 3c is a much shorter distance due to a higher bias voltage being applied. These distances can be compared to long and short strings which are held by the ends and then plucked. The long, relaxed string will vibrate at a much lower frequency when plucked than will the shorter, tighter string. Analogously, the resonant frequency of the CMUT cell in FIG. 3a will be lower than the resonant frequency of the CMUT cell in FIG. 3c which is subject to the higher pulldown bias voltage.

Figure 3D:
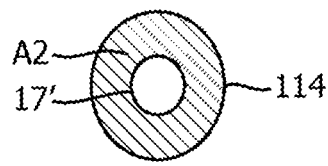

The phenomenon can also be appreciated from the two-dimensional illustrations of FIGS. 3b and 3d, as it is in actuality a function of the effective operating area of the CMUT membrane. When the membrane 114 just touches the floor of the CMUT cell as shown in FIG. 3a, the effective vibrating area A1 of the non-contacting (free vibrating) portion of the cell membrane 114 is large as shown in FIG. 3b. The small hole in the center 17 represents the center contact region of the membrane. The large area membrane will vibrate at a relatively low frequency. This area 17 is an area of the membrane 114, which is collapsed to the floor of the CMUT cell. But when the membrane is pulled into deeper collapse by a higher bias voltage such as in FIG. 3c, the greater central contact area 17' results in a lesser free vibrating area A2 as shown in FIG. 3d. This lesser area A2 will vibrate at a higher frequency than the larger A1 area. Thus, as the DC bias voltage is decreased the frequency response of the collapsed CMUT cell decreases, and when the DC bias voltage increases the frequency response of the collapsed CMUT cell increases.

Figure 4:
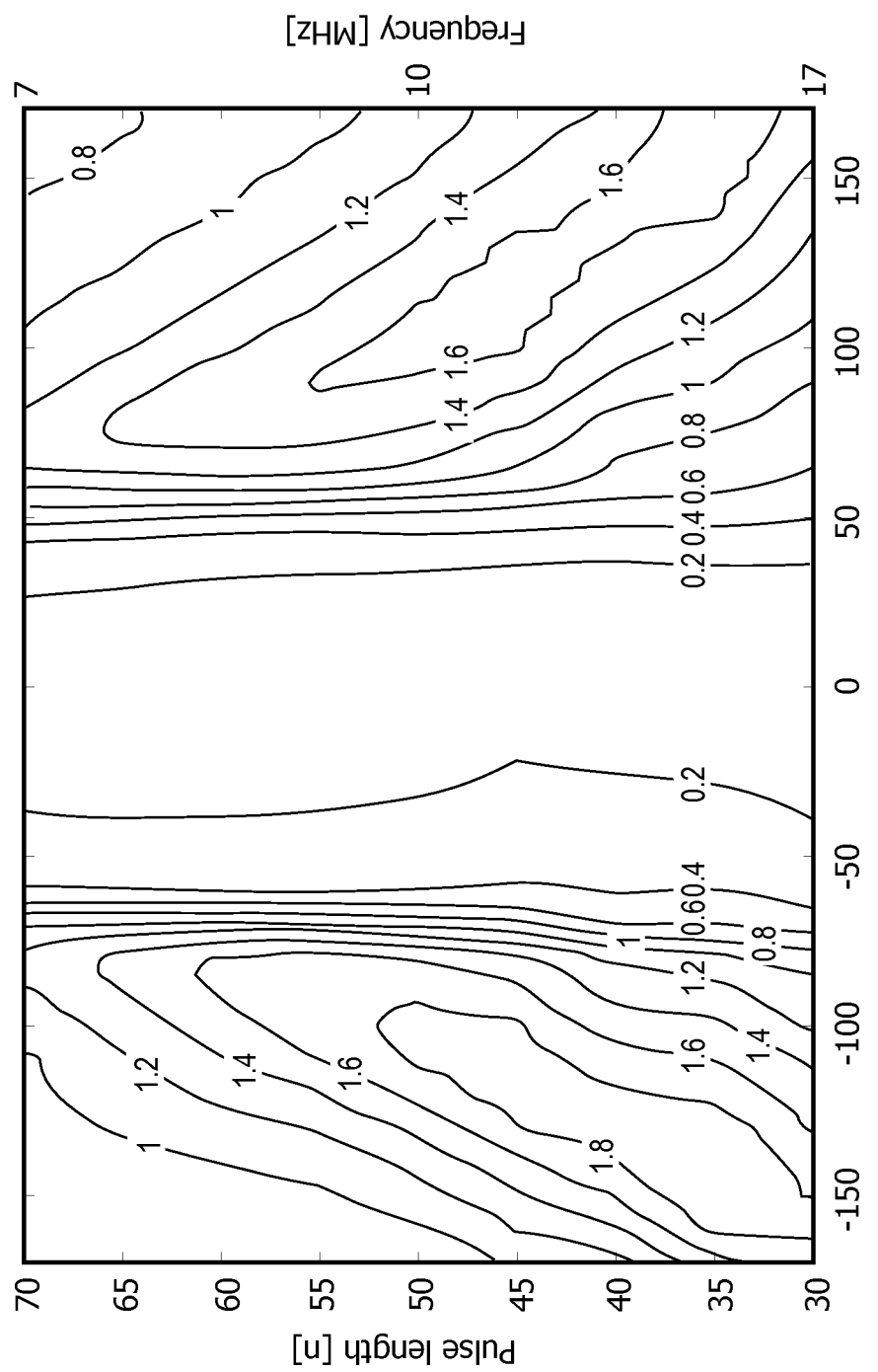
FIG. 4 illustrates a contour plot of the acoustical performance of such the CMUT cell operating in collapsed mode.

FIG. 4 shows a contour plot of the acoustical pressure output of a typical CMUT cell 103 in collapse mode as a function of applied DC bias voltage including a stimulus in the form of an AC modulation or frequency modulation of constant frequency during transmission. The corresponding pulse length is half the applied frequency. As can be seen from this contour plot, when the CMUT cell 103 is operated at a fixed or static voltage, e.g. a DC bias voltage of static value, optimal acoustic performance is obtained for a small range of frequencies only. However, when varying the bias voltage and the frequency modulation on the bias voltage signal in a correlated manner the optimal acoustic performance of the CMUT cell 103 may be achieved over a much larger frequency range, thereby increasing the effective bandwidth of the ultrasound pulse (or pulse train) generated in the transmission mode of the ultrasound probe including the CMUT cell 103. Thus, frequency can be varied in a frequency range from 7 to 17 MHz, as in this example; 3 to 10 MHz; or even larger frequency range expanding from 2 to 15 MHz.

This can be understood in back reference to FIGS. 3a and 3d, which explained that the resonance frequency of the CMUT cell 103 in a collapsed state is a function of the applied (DC) bias voltage. By adjusting the applied bias voltage when generating ultrasonic pulses of a particular set frequency by applying a stimulus having the appropriate set frequency, pulses of different frequencies can be generated exhibiting (near-)optimal acoustic performance of the CMUT cell 103 for each pulse frequency. This therefore ensures (near-) optimal imaging resolution over a large bandwidth of the imaging spectrum.

Acoustic wave attenuation increases with increasing frequency, while ultrasound image resolution reduces with increasing frequency. For example, a typical depth and axial resolution for a two-cycle pulse in tissue is given in the table below:

| Frequency (MHz) | Image depth (cm) | Axial resolution (mm) |
| --- | --- | --- |
| 2 | 30 | 0.77 |
| 5 | 12 | 0.31 |
| 7.5 | 8 | 0.2 |
| 10 | 6 | 0.15 |
| 15 | 4 | 0.1 |

To meet optimal and penetration requirements reasonably, the frequency range for most diagnostic applications is 2 to 15 MHz. The lower portion of the range is useful when increased depth (e.g., the region of interest is located deeper in body) or high attenuation (e.g., in transcranial studies) is encountered. The higher portion of the frequency range is useful when little penetration is required (e.g. in imaging breast, thyroid, or superficial vessel or in pediatric imaging). In most large patients, 3-5 MHz is a satisfactory frequency, whereas in thin patients and in children, 5 and 7.5 MHz often can be used. A higher frequency range above 15 MHz can provide high resolution imaging using intracavity (intravascular) probes, such as IVUS, ICE, FL-ICE. These probes can be positioned closer to the ROI inside body cavities, vessel, etc. However, although the use of CMUT arrays 14 might be beneficial in some embodiments, it is reiterated that any suitable type of array 14 may be used in the context of the present invention, as explained above.

In accordance with the present invention, the ultrasound system 100 is extended with so-called 'anatomical intelligence'. Anatomical intelligence in ultrasound imaging interprets the patient's ultrasound data and applies adaptive system intelligence using (3D) anatomical models to create easier and more reproducible results. Anatomical intelligence tools may deploy advanced organ modeling, image slicing, and proven quantification to help make ultrasound exams easier to perform and more reproducible while improving and extending the generated clinical information, thereby extending the functionality of the ultrasound system 100.

In the context of the present application, 'anatomical intelligence' includes the ability of the ultrasound system 100 to identify an anatomy to be imaged and to identify anatomical features of interest, e.g. a ROI, within ultrasound imaging data provided by the probe 10. For example, the ultrasound system 100 may be adapted to apply an appropriate anatomical model to the ultrasound imaging data, such as for example a heart model that can identify the structure of a patient's heart in the ultrasound imaging data and follow changes in the heart's geometry, e.g. to extract functional cardiac parameters such as ejection volume or the like from a sequence of ultrasound images visualizing the cardiac cycle. The anatomical model of the present invention can also be based on various machine learning algorithms, such as algorithms combining machine training with a biomechanical model of the anatomy.

Examples of the anatomies to be imaged using the disclosed ultrasound system may include liver, fetus (obstetric application of ultrasound imaging), lungs, carotid and pancreas.

An embodiment of the obstetric application may include configuring the ultrasound system to identify a presence of a fetus (as the identified region of interest) and its crown-rump length (in case the crown-rump measurement procedure is selected). Another example of the obstetric ultrasound medical use case is a confirmation of the fetal cardiac pulsation; in this case the identified anatomical features of interest is a location of the fetal heart.

An embodiment of vascular ultrasound assessment can be ultrasound imaging of the carotid. In the vascular ultrasound imaging often, next to B-mode imaging, Doppler imaging mode is used. Since an error for Doppler angle identification can be reduced for a specific range of angles between ultrasound beams and vessel flow, the ROI identified of the described system would take the optimal range of angles between ultrasound beams and vessel flow into account in order to generate the identification data indicating the region of interest.

Further, such anatomical intelligence may be particularly advantageously applied to ultrasound systems used for interventional procedures, as the anatomical intelligence, and in particular the ability to identify a ROI to which the interventional procedure is to be applied may be leveraged. Non-limiting examples of such interventional application domains include intra-vascular ultrasound (IVUS), intra-cardiac echocardiography (ICE) and transesophageal echocardiography (TEE). IVUS is typically used in intra-vascular ultrasound workflows during which arterial wall abnormalities are assessed.

For example, an arterial wall plug (atheroma) may be identified as a ROI and accessed by an IVUS probe 10, where the probe 10 may be guided towards the ROI in an automated fashion or by a user receiving guidance instructions from the ultrasound system 100 based on the ROI identification as explained in the present application.

As another example, an ICE catheter or TEE probe 10 may be used in heart intervention procedures such as transseptal crossing or puncture in which the catheter punctures the septum in between the two atria or trans-catheter aortic valve repair (TAVR) procedures. Of course, non-interventional procedures such as automated cardiac quantification (commonly used in 2D), e.g. heart chamber volume estimation or ejection fraction estimation may also benefit from such anatomical intelligence-assisted imaging.

It is further noted that the ROI is not necessarily merely an anatomical feature. In an embodiment, the probe 10 may be used to image an interventional device such as a catheter or the like, in which case the location of the interventional device within the patient's anatomy can become the ROI within the ultrasound imaging data. For example, in a scenario where a separate interventional tool such as a catheter is to be imaged within the heart, the ultrasound system 100 may be configured with knowledge as to the required positioning of the probe 10 within the heart to facilitate appropriate imaging of the interventional tool to support a subsequent interventional procedure, which required positioning may be verified by identification of one or more ROIs within the heart as a check whether the probe 10 is positioned correctly to image the interventional tool, with the anatomical intelligence further providing knowledge to the ultrasound system 100 that the probe 10 is to visualize (and track) the interventional tool from its target position.

As mentioned earlier, the anatomical intelligence may be utilized to assist guidance of the probe 10 (or a catheter), towards the ROI, either automatically or by providing the user of the probe 10 with guidance instructions based on the ROI detection. As a non-limiting example, in a procedure in which the probe 10 is to image the left ventricle of a patient's heart, the user may be presented with guidance instructions, e.g. audible instructions or visual instructions displayed on the display 18, ensuring that the probe 10 is guided into the right ventricle by the user in order to facilitate appropriate imaging of the left ventricle. In an embodiment, which will be explained in more detail below, the guidance instructions may be generated by the ultrasound system 100, e.g. by the ROI identifier 72, by the image processor 68 or by any other suitable component of the system, based on a ROI evaluation of the ROI identifier 72.

For example, the actual anatomical intelligence use case may specify a target location and/or a target distance from the ROI for the probe 10, with the ROI identifier 72 being adapted to determine the actual location and/or actual distance of the probe 10 relative to the ROI. The image analyses unit 68' may be arranged, based on the identified use case in association with said use case's anatomy model, to assess an optimal ultrasound wave transmission applicable for the given probe's location. If no optimal configuration can be achieved, for example the ROI is too far (or non-optimally located within the field of view) for performing diagnoses, defined by the medical procedure, based on the acquired ultrasound image data, this actual position information may be leveraged by the ultrasound system 100 to generate guidance instructions for the controller of the probe 10, which may be a person or a drive mechanism 21 to be explained in more detail below, in order to guide the probe 10 from its present location to the target location. The ROI identifier 72 may provide regular feedback during the guidance of the probe 10 towards its target location as specified in the use case, to ensure that the probe 10 is correctly positioned, e.g. to perform an interventional procedure or to successfully image a further interventional tool as explained above.

In case such guidance instructions are presented to an operator of the probe 10, they may be presented in any suitable manner, e.g. as audible instructions and/or as visual instructions on the display 18. Such visual instructions may be presented in any suitable form, e.g. as text instructions or as graphical instructions presented within the volumetric image captured by the probe 10 as displayed on the display 18, e.g. as a coloured overlay of this image to highlight the trajectory the probe 10 should follow towards its target location. Other suitable visualization of such guidance instructions will be immediately apparent to the skilled person.

The ultrasound system 100 may be configured with such anatomical intelligence in any suitable manner. For example, the ultrasound system 100 may be programmed with a plurality of use cases, each use case for example comprising workflow steps that will guide a user through the correct operational procedure, e.g. an obstetric, IVUS or ICE procedure, as well as an anatomical model appropriate for that use case, which anatomical model for example may include one or more segmentation algorithms to facilitate automated detection of the ROI in the ultrasound image data generated by the probe 10. To this end, the ultrasound system may comprise or may be connected to a data storage arrangement (not shown) from which the appropriate use case may be retrieved upon its identification as explained in more detail below.

Optionally, each use case may further include at least one of navigation instructions for navigating the probe 10 through the anatomy of the patient, in case of at least partially manual navigation required for the particular procedure, and tracking algorithms for tracking a moving object such as an interventional device through the patient's anatomy when the probe 10 is in its intended location for such tracking. The programming of the ultrasound system 100 may be performed in any suitable manner, e.g. by a user manually programming the ultrasound system 100 through the user interface 38, by the user invoking a download of the use cases from a remote use case database, e.g. over a network such as the Internet in any suitable manner, and so on.

In an embodiment, the ultrasound system 100 is configured to automatically select the appropriate use case in order to provide automated ROI detection, automated configuring of the ultrasound wave transmission and user guidance during use of the probe 10. This for example may be achieved by including a tag or the like in a plug 22 of a cable 20 attached to the probe 10 for connecting the probe 10 to a user console 24 or the like of the ultrasound system 100. Such a tag may include an identifier of the probe 10 and/or its appropriate use case, from which the ultrasound system 100 can derive this use case. Such a tag may be read in any suitable manner, e.g. through a connection pin of the plug or through using near field communication between an RF tag and a tag reader located proximal to the socket of the user console or the like into which the plug is inserted. Other suitable ways of obtaining the identification information from the tag will be immediately apparent to the skilled person. This embodiment is particularly suitable for probe types used for a single, specific application, such as for example IVUS probes.

Alternatively or additionally, the ultrasound system is configured to select the appropriate use case in response to a user input identifying the appropriate use case, which user input may be provided in any suitable manner, e.g. via a touchscreen display 18 and/or a user interface 38. This for example may be desirable in scenarios in which a probe 10 may be used in different procedures, such as for example is the case for an obstetric, ICE or TEE probe, which may be used in different cardiac procedures such as ablation (with septum crossing), valve replacement or interventional tool tracking as explained above.

In an example embodiment, the ultrasound system configurable with the various procedural use cases as explained above provides a unique combination of a variable frequency ultrasound imaging in a broad frequency range using a single array 14 of CMUT transducers.

FIG. 5 illustrates a basic principle of this example embodiment with a fixed probe's position with respect to the ROI 82'. The probe 10 is used to acquire ultrasound images of the volumetric field of view 131. The transducer frequency controller 62 is responsive to the region of interest identifier 72 sets a relatively low frequency of the ultrasound beams steered within the volumetric field of view 131 and a relatively high frequency of the ultrasound beams steered within the volumetric region 132 surrounding the identified ROI 82'. The received by the CMUTs echoes are processed by the beamformer, which provides the ultrasound image data of the volumetric region having a relatively low spatial resolution within the volumetric region outside of the ROI and relatively high spatial resolution within the region of interest. These ultrasound data are processed in the image processor 68, wherein a wide view 80 of the volumetric region based on the low spatial resolution data and a detail view 132' of the region of interest 82 based on the high spatial resolution data are produced as shown in FIG. 6. The detail view 132' of the volumetric region 132 surrounding the identified ROI 82 may also comprise an image 133 of the area located in between the probe and the ROI.

In this non-limiting to the CMUT array example, the ultrasound wave controlling unit 64' can be also adapted to vary a density of the ultrasound beams steered within the volumetric region, said density being defined by the selected imaging procedure. The ultrasound wave controlling unit is responsive to the region of interest identifier 72 sets a relatively low density of the ultrasound beams steered within the volumetric field of view 131 and a relatively high density of the ultrasound beams steered within the volumetric region 132 outside the identified ROI 82'. Further, the ultrasound wave controlling unit 64' can adapted to vary a steering angle of the ultrasound beams within the identified ROI (often applicable for Doppler imaging procedures).

FIG. 6 illustrates a display 99 of 2D ultrasound images displayed to the user with the wide view 80 and the detail view 132' in spatial registration with respect to each other. A representation 82 of the selected ROI 82' is displayed at the increased imaging frequency (or increased image frame rate) in the detail view 132'. Since the penetration depth of the ultrasound beams with relatively high frequency is reduced compared to the penetration depth of the ultrasound beams with the relatively low frequency, an upper frequency limit of the relatively high frequency range will be limited by a depth (distance to the probe) at which the ROI is located and will be taken into account by the image processer 68 during its computation. The system 100 may first acquire ultrasound data of the volumetric field of view with the relatively low beam frequencies (or low steered beam density), thus providing surrounding context of the volumetric region, and further "zoom-in" to the ROI 82 upon its identification. The detail view 132' of the ROI 82 can be updated in the real time next to the wide view 80 acquired previously and displayed for the context as illustrated in FIG. 6c.

Alternatively, the detail view 132' of the ROI 82 and the wide view 80 can be displayed next to each other. In cardiology application during heart imaging the display and acquisition of the ultrasound images may be synchronized with heart cycle by an ECG gating.

In case the CMUT array 14 is a linear array the transducer frequency controller 62 can address (drive) the individual transducer cells 103 with different frequencies so that the ROI is imaged at high frequency and that the other elements are maintained at low frequencies. A representative image acquired with the linear array is shown in FIG. 6b.

An embedded real time high frequency detail view 132' image is generated simultaneous to a real time low frequency wide view 80 image. This has the advantage that the surrounding context is still imaged (albeit at lower resolution) in real time with relatively higher depth to allow for example orientation and navigation of tools that occur in the periphery of the ROI. It is also possible to obtain similar images if the CMUT array 14 is a phased array as shown in FIG. 6a and FIG. 6c. In the phased array case the beamforming is performed such that for each line that constitutes the image, an appropriate frequency for all the transducers is chosen such that a high frequency detail view 132' image is imbedded in the wide view 80 image containing lower frequency lines. If both views: the detail view 132' of the ROI 82 and the wide view 80 are updated in real time, the system comprising the phased array can continually acquire first all lines of the volumetric field of view 131 volume at low frequency and then all lines the volumetric region 132 surrounding the identified ROI 82 with higher frequency. The acquired view can by further interleaved or interpolated into one ultrasound image. This is illustrated in FIG. 6c. In alternative acquisition workflow the wide view 80 is updated beyond detail view 132', wherein the resulting image displayed to the user is illustrated in FIG. 6a. The former has the advantage of real time views of the whole volume e.g. to track interventional devices in certain procedural use cases as explained above. The latter has the advantage that fewer lines are acquired and a higher frame rate can be achieved.

Figure 7:
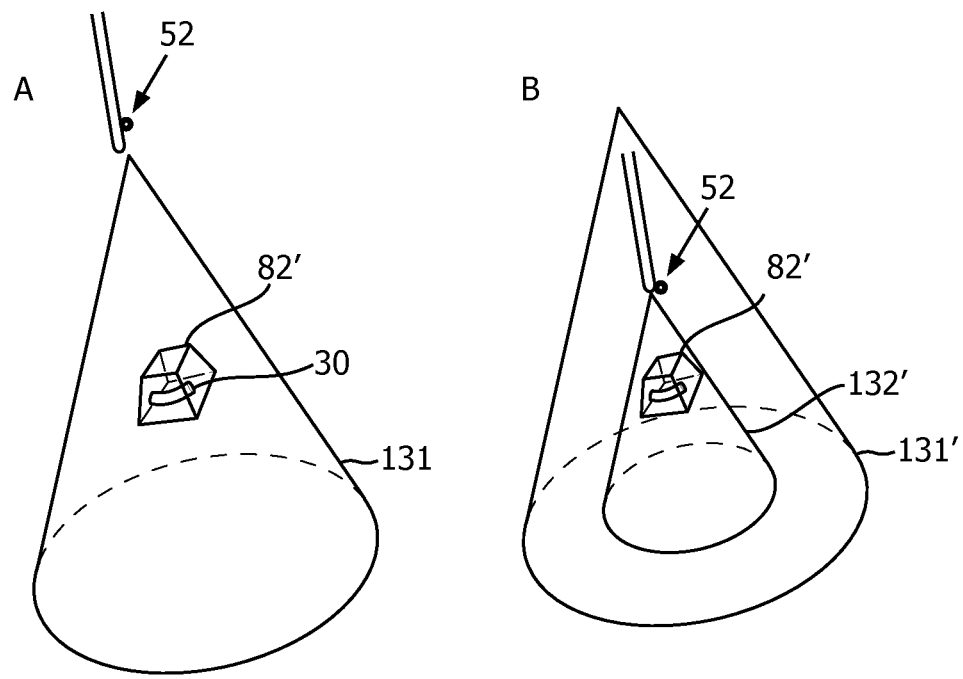
FIG. 7a-b illustrates the scanning of the volumetric region with variable beam frequency using an intracavity probe adapted to be moved with respect to the volumetric region.

FIG. 7 illustrates a particularly advantageous embodiment of the present invention, wherein the probe's position can be varied within the volumetric field of view 131'. The probe, for example, can be placed in a forward looking or end firing configuration such that the probe can be easily translatable towards and away from the ROI. This can be realized by providing the intracavity probe such as IVUS (intravascular ultrasound), ICE (intracardiac echocardiography), FL-ICE (forward looking intracardiac echocardiography), for example as described in EP1742580B.

Figure 9:
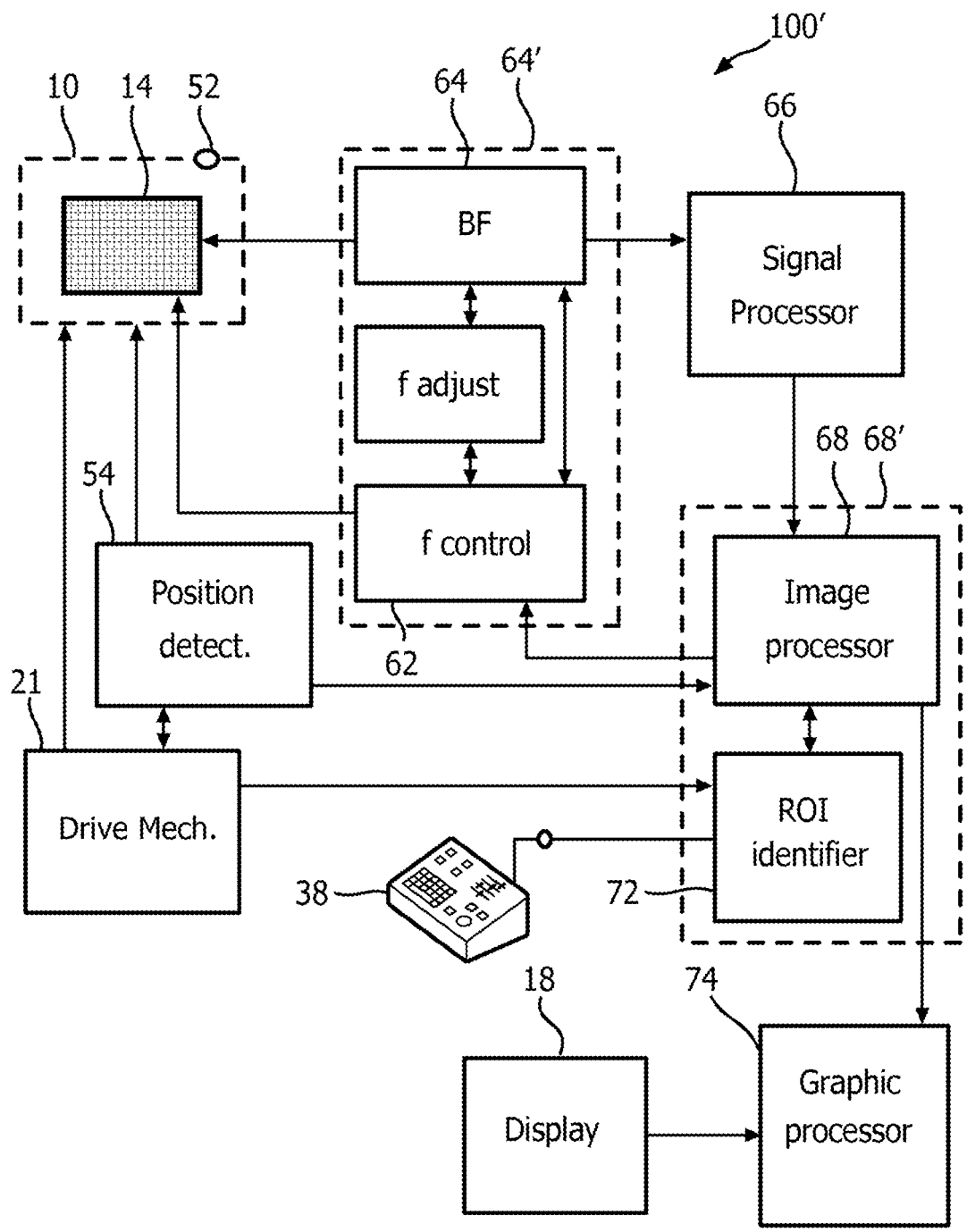
FIG. 9 illustrates an ultrasound system for imaging a volumetric region comprising a region of interest in accordance with an example embodiment of the present invention.

The intracavity probe may include the transducer array in the distal tip which is swept to scan a volumetric region. The volume sweeping can be done either providing a mechanical movement of the 1D array or an electronic steering of the beams with the 2D array. The transducer array is contained within a fluid chamber located at the distal tip of the probe, wherein fluid provides an appropriate acoustic coupling between the probe and the imaged volumetric region. In FIG. 9 the ultrasound system 100' of the present invention is schematically shown. The system 100' may further comprise a drive mechanism 21 coupled to the probe and the ROI identifier 72 (optionally to the analyses unit 68'), wherein the drive mechanism based on the identification data acts to move the probe 10 during imaging. The drive mechanism 21 may also receive the signals from the position sensor 52, which tracks the probe's spatial location, thus providing an independent verification of the probe's movement within the volumetric field of view 131'. This embodiment gives a higher flexibility to the upper limit of the high frequencies with which the ROI 82' can be imaged in case the probe 10 deploys CMUTs. Once the ROI is identified the image processor 68 computes coordinates of the ROI 82 and a volumetric region 132 surrounding the identified ROI in the volumetric field of view 131 based on the identification data obtained using the anatomical model of the selected use case as explained above. The ROI identifier may determine the distance between the probe 10 and the region of interest, and may decide if the probe 10 needs to be adjusted, either to obtain a better view of the ROI or to move the probe 10 into a target position as specified by the selected procedural use case as explained above. For example, in case of a CMUT array 14, if the distance between the transducer array 14 (or practically the probe 10) and the ROI is beyond the penetration depth of the beams with the selected high frequency, the drive mechanism 21 would be communicated to move closer towards the ROI within the volumetric field of view 131' (FIG. 7b), such that a "zoom-in" image of the ROI can be acquired, or to move the probe 10 closer to a target location relative to the ROI as specified in the selected use case. Similarly, a "zoom-out" may be implemented in case the ROI cannot be fully imaged or if the probe 10 is too close to the ROI as per the use case specification of its target location, in which case the drive mechanism 21 would be communicated to move away from the ROI within the volumetric field of view 131'. Alternatively, an operator of the probe 10 may be provided with guidance instructions to move the probe 10 accordingly, as previously explained.

This invention combines benefits of the addition of anatomical intelligence to an ultrasound system 100 in order to facilitate the guiding of the probe 10 to a target location, wherein an optimal ultrasound image of the ROI can be acquired, that is appropriate for a particular imaging procedure. Preferably, an automated zooming-in and out function within the volumetric region is provided by a feedback loop from the ROI identifier 72 to the driving device 21, thereby providing a user with a new generation of ultrasound systems. In a specific embodiment, miniaturized CMUT transducers (enabled by advances in CMOS manufacturing) and their broad operation band (enabled by the collapsed mode of operation) are deployed such that a combination of the wide frequency band of the CMUT array operating in the collapsed mode with means to physically translate the probe comprising this array enables a new user experience in advanced ultrasound imaging with increased details and therefore improved diagnostic imaging.

Figure 8:
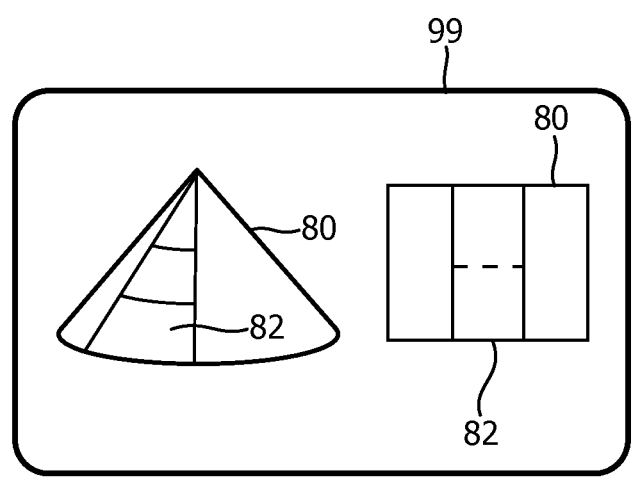
FIG. 8 illustrates display of ultrasound images obtained with an intracavity probe in accordance with the principles of an example embodiment the present invention.

FIG. 8 illustrates a display 99 of 2D ultrasound images displayed to the user. The detail 82 and wide views 80 may be shown either next to each other or in a spatial registration. The latter case is illustrated in FIG. 8, wherein the images obtained with the linear and phased arrays are placed next to each other. Compared to FIGS. 6a-b the detail view 82 would appear to the user as having a larger penetration depth compared to the embodiment, wherein the probe's position is fixed with respect to the ROI's location. The detail view image can be continuously acquired during the probe's progression (movement), such that the wide view image 80 can be real-time updated with higher resolution detailed view images 82 acquired at different points of time. In addition, a current position of the moving probe within the volumetric region can be displayed in the wide view image 80.

Based on the ROI identification and the use case-identified parameters the image processor 68 may analyze the obtained ultrasound data for image quality parameters such as axial noise, lateral speckle, axial intensity etc. These quality parameters may be further displayed to the user. These quality parameters can also be used as an input to the drive mechanism to automatically move the probe so that it can be part of a feedback loop for automatic optimization of the ROI image quality and/or positioning of the probe 10 in a use case-specified location as previously explained. Such automation may be used for a fine movement of the probe, while the gross motion can be controlled via the user interface 38, to which end the user may be presented with guidance instructions as previously explained. Via the user interface 38 the user can be provided an additional control on the drive mechanism operation. The user interface can be a touch screen associated with the display 18, which permits the user to manually define in a displayed image the ROI and/or probe's movement. Touching on the ROI and/or making the "pinch-in" or "pinch-out" movement can be used to physically move the probe in a certain direction(s) or acquires the detailed image if the penetration depth is sufficient for the given probe's position.

In an alternative embodiment a real time detailed 3D field of view of the ROI obtained with relatively high frequency is imbedded within a wide view 2D image. This has the advantage that acquiring the wide view 2D image consumes less processing power and transducer utilization and that the 3D image (or biplane ROI) can be obtained at the highest possible frame rate. For the arrays with small aperture in one dimension (e.g., ICE), this embodiment provide the wide view imaging based on the more favorable aperture dimensions (ICE axial, and lateral) and the detailed ROI imaging at all dimensions (e.g. ICE: including elevation), which becomes more favorable at high frequency.

The ROI identifier can identify the ROI automatically using ultrasound data from a specific object such as a catheter, needle or tool, e.g. using an anatomical model of a selected anatomical intelligence use case, which can optionally be marked with ultrasound enhancing contrast features. These objects by virtue of their geometry and aspect (or markers or positional sensor) can be recognized by the image analyses unit 68' and the coordinates of the ROI can be automatically generated.

In another embodiment an image of a volume of interest can be acquired initially with relatively high frequency beams, this volume of interest can be identified by the user as the ROI. Further, the user via the user interface can decrease the imaging frequency, relative to what was used for the ROI, in order to obtain a wide view image with higher penetration depth, wherein the wide view image comprises the ROI. Similar to previous embodiments these fields of view may be displayed either next to each other or in the spatial registration.

Separate requirements may be imposed onto an integrated circuit (IC) electronics of the ultrasound wave controlling unit 64' (or optionally of the transducer frequency controller 62) in order to provide an optimal speed of the bias-voltage change applied to the CMUTs. For most instances described above current IC electronics technology may be sufficient. Alternatively, in case even larger speed of the bias-voltage change is needed the 3-terminal CMUT as described in WO/2015/086413 in may be used.

In FIG. 10 illustrates a workflow 200 of a basic principle of variable ultrasound wave image acquisition. At step 201 the volumetric field of view 131 is imaged this field of view comprises the wide view 80. In step 202 the ROI 82 is detected by the identifier, the automatic detection can be performed based on distinguishing anatomy feature 30, for example, or based on the selected procedural use case with anatomical intelligence. In step 203 outlines of the ROI may be displayed to the user. At this stage the user can also manually interact via the user interface 38 with the systems 100 adjusting the size and/or location of the ROI. Further, in step 204 the user can select the desired resolution (or frequency) and/or frame rate of the detail view of the ROI. The image processor 68 further translates the selected resolution into the transducer operation frequency or steered beam density. Alternatively, in this step the image processor 68 can compute an upper frequency limit (or lower limit of beam density), with which the ROI 82 can be imaged based on the fixed distance from the probe 10 (namely the transducer array 14 within the probe) to the ROI. This information may be displayed on the display. In step 205 the system 100 would acquire the detail view of the ROI with increased resolution (or frame rate). In step 206 the wide and detailed fields of view are displayed to the user.

In FIG. 11 illustrates a workflow 300 for ultrasound wave image acquisition in accordance with an example embodiment of the present invention. At step 301 the volumetric field of view 131 is acquired. In step 302 the ROI 82 is detected by the identifier using the anatomical model associated with the selected anatomical intelligence use case of the present medical procedure. In step 303 outlines of the ROI may be displayed to the user. At this stage the user can also manually interact via the user interface 38 with the systems 100' adjusting the size and/or location of the ROI. In parallel, in step 307 the image processor 68 computes the distance from the probe to the most distant edge of ROI. Further, in step 304 the user can select the desired resolution (or frequency) and/or frame rate of the detail view of the ROI. In step 309 Based on this information the image processor 68 computes the penetration depth corresponding to the selected resolution (frequency). In step 308 the distance between the probe and the ROI is compared to the penetration depth. If the computed penetration depth is larger than the distance to the ROI, then the workflow is followed by step 305, in which the system 100 acquires the detail view of the ROI with the selected resolution. If the computed penetration depth is smaller than the distance to the ROI, then the workflow is followed by step 310, in which the drive mechanism provides probe's movement towards the ROI's location. A movement distance is determined by the ROI location and the selected resolution. In case the movement distance is limited by an anatomy of the imaged volume (object), such that the probe cannot be moved further, the system 100' may provide a feedback to the user with a computed optimal resolution at which the ROI can be acquired taking into account anatomy limitations. Further, system 100 acquires the detail view of the ROI with the selected resolution or optimal suggested resolution in step 305. In step 306 the wide and detailed fields of view are displayed to the user. Alternatively, the distance between the probe 10 and the ROI may be compared against a target value provided by the selected use case, in which case guidance instructions for the user of the probe 10 or the drive mechanism 21 may be generated in order to guide the probe 10 to its target location relative to the ROI as explained in more detail above. It is once more noted that although FIG. 11 is described in the context of CMUTs, other types of transducers equally may be deployed.

Figure 12:
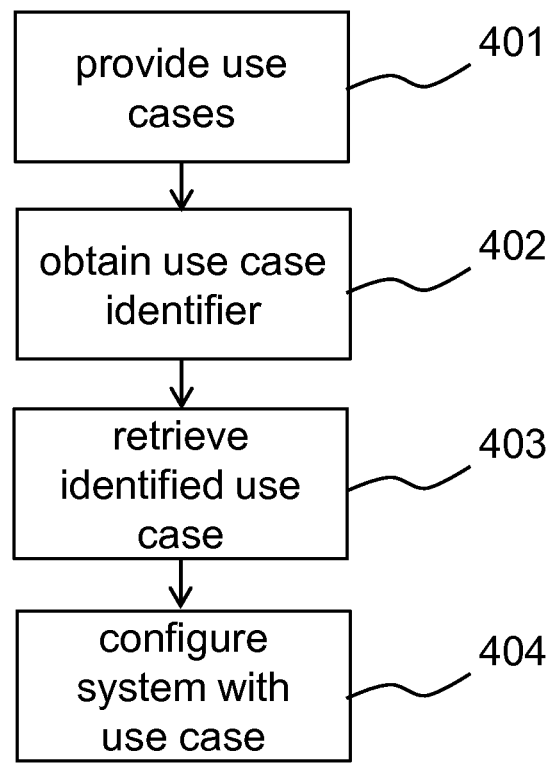
FIG. 12 illustrates a workflow of configuring an ultrasound system in accordance with the present invention.

FIG. 12 is a flowchart of an embodiment of a method 400 of configuring the ultrasound imaging transmission of the ultrasound system 100 with a procedural use case to impart the appropriate anatomical intelligence onto the ultrasound system 100. In operation 401, a plurality of use cases is provided, each defining the anatomical intelligence to be imparted onto the ultrasound system 100, such as the anatomical model to be deployed by the ROI identifier 72 as well as acceptable quality of the ultrasound imaging data in a particular imaging procedure, e.g. an obstetric, ICE, FL-ICE or IVUS procedure. As explained in more detail above, such use cases may further comprise configuration parameters for the ultrasound system 100, e.g. for the beamformer 64, the image processor 68, the drive mechanism 21 and so on, such that the ultrasound system 100 can be automatically configured by such use cases, thereby significantly reducing the required user interaction with the ultrasound system 100 in order to appropriately set up the system for a particular interventional procedure. This therefore makes the use of such ultrasound systems 100 for such procedures more accessible to less experienced users.

In operation 402, the ultrasound system 100 receives the identifier of a particular use case, e.g. from a user through the display 18 in case of a touchscreen display or through the user interface 38, or from automatic detection of a tag in the plug of the probe 10 to be inserted in a user console of the ultrasound system 100 as previously explained, which identifier is used by the ultrasound system 100 to retrieve the use case identified by the received identifier from a data storage device, e.g. a data storage device of the ultrasound system 100 or a remote data storage device accessible over a network such as the Internet in operation 403. Finally, the ultrasound system 100 configures itself and its ultrasound wave transmission, e.g. the ROI identifier 72, with the retrieved use case in operation 404, thereby providing at least a semi-automated configuration of the ultrasound system 100 in accordance with an imaging procedure to be performed with the probe 10.

It shall be understood by the person skilled in the art that the principles of the present invention can be practiced in both 2D and 3D ultrasound imaging.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

In the foregoing, where reference is made to an ultrasound system 100, it should be understood that such a system may be provided without the ultrasound probe 10, e.g. as an ultrasound system module such as a user console that, when connected to a suitable ultrasound probe 10 forms any embodiment of the present invention as described herein.

The invention claimed is:
1. An ultrasound system for imaging a volumetric region comprising a region of interest, said system comprising:
  a probe comprising an array;
  an ultrasound wave controlling unit coupled to the array and adapted to control ultrasound wave transmission by the array and provide ultrasound image data of the volumetric region;
  an image processor responsive to the ultrasound image data, based on which it is adapted to produce an ultrasound image;
  a region of interest (ROI) identifier configured to identify a region of interest on the basis of the ultrasound image data, and which ROI identifier is adapted to generate identification data indicating the region of interest within the volumetric region;
  a user interface;
  wherein the ultrasound wave transmission within the volumetric region is configurable by a plurality of use cases in response to respective identification data of said use cases, each use case being associated with a particular imaging procedure and comprising: (i) an anatomical model for said imaging procedure; and (ii) one or more configuration parameters for the ultrasound system for said imaging procedure, and com- prising guidance instructions for assisting a user of the probe in guiding the probe to a target location;

wherein the ultrasound system is configured to receive, from the user via the user interface, a particular use case identifier configured to identify a particular use case;

wherein the ultrasound system is configured to, in accordance with the particular use case identified by the particular use case identifier: (1) automatically configure the ultrasound wave transmission; (2) provide guidance instructions; and (3) provide automated ROI detection, wherein the ROI identifier is configurable by the respective anatomical models of said use cases;

wherein automatically configuring the ultrasound wave transmission comprises automatically varying, by the ultrasound wave controlling unit in accordance with the particular use case identified by the particular use case identifier, a frequency of the ultrasound waves transmitted within the ROI and the volumetric region surrounding the identified ROI;

wherein the image processor is configured to analyze, based on the particular use case identifier and the ultrasound image data, one or more image quality parameters, and wherein the ultrasound system is configured to automatically adjust, based on the analyzed one or more image quality parameters, the probe to optimize the ultrasound image data for the particular use case, wherein the ultrasound wave controlling unit further comprises a beamformer adapted to control ultrasound beam steering of the transmitted ultrasound wave; and wherein the ultrasound beam steering is adapted to be configured by the plurality of use cases in response to the respective identification data of said use cases, wherein the probe comprises an array of capacitive micromachined ultrasonic transducer (CMUT) transducers adapted to steer ultrasound beams in a variable frequency range over the volumetric region; and the ultrasound system further comprises a transducer frequency controller coupled to the beamformer and adapted to vary operation frequencies of the CMUT transducers within the frequency range; which frequency controller is arranged to set the operation frequency to a first frequency for the ultrasound beam steered in the volumetric region, wherein the transducer frequency controller is further adapted to change, based on the identification data, the operation frequency to a second frequency for the ultrasound beams steered within the region of interest, the second frequency being higher than the first frequency; and a drive mechanism coupled to the probe, wherein the drive mechanism is adapted to move the probe, based on the identification data, enabling a distance variation between the probe and the ROI.

2. The ultrasound system according to claim 1, wherein the transducer frequency controller is adapted to simultaneously set, the operation frequency to the second frequency for the ultrasound beams steered within the ROI and to the first frequency for the ultrasound beams steered outside the region of interest, the second frequency being higher than the first frequency.

* * * * *